United States Patent [19]

Di Domenico et al.

[11] Patent Number: 4,849,437
[45] Date of Patent: Jul. 18, 1989

[54] 2-SULPHINYL-ACETYL-1,3-THIAZOLIDINES, THEIR PREPARATION AND PHARMACEUTICAL COMPOSITIONS

[75] Inventors: Roberto Di Domenico; Daniele Castoldi; Silvano Spinelli; Odoardo Tofanetti; Sergio Tognella; Carmelo A. Gandolfi, all of Milan, Italy

[73] Assignee: Boehringer Biochemia Robin S.p.A., Milan, Italy

[21] Appl. No.: 181,536

[22] Filed: Apr. 14, 1988

[30] Foreign Application Priority Data

Apr. 17, 1987 [IT] Italy ................ 20179 A/87

[51] Int. Cl.$^4$ ................ C07D 277/04; A01K 31/425
[52] U.S. Cl. .................... 514/365; 548/200
[58] Field of Search ............ 548/200; 514/365

[56] References Cited

U.S. PATENT DOCUMENTS 4,477,458 10/1984 Mora ................ 548/200

Primary Examiner—Robert Gerstl
Attorney, Agent, or Firm—Armstrong, Nikaido Marmelstein Kubovcik & Murray

[57] ABSTRACT

Thiazolidines of formula I

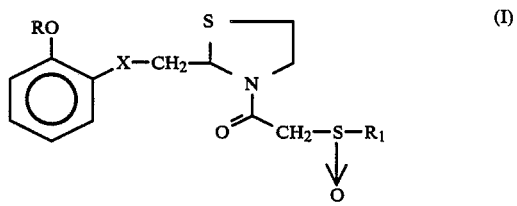

wherein
R is H, $C_1$–$C_4$-alkyl, allyl or propargyl;
X is O, $CH_2$, S;
$R_1$ is $C_1$–$C_6$-linear or branched alkyl, phenyl, benzyl, or a group of formula $CH_2$—$CH_2$—O—($CH_2$—$CH_2$—O)$_n$—Ra wherein n is zero or an integer from 1 to 3 and Ra is H, benzyl or $C_1$–$C_6$-linear or branched alkyl.

Compounds I are endowed with favourable therapeutical properties for pathologies of the respiratory system.

5 Claims, No Drawings

2-SULPHINYL-ACETYL-1,3-THIAZOLIDINES, THEIR PREPARATION AND PHARMACEUTICAL COMPOSITIONS

The present invention refers to 2-sulphinyl-acetyl-1,3-thiazolidines, a method for their preparation and pharmaceutical compositions containing them.

The compounds of the invention have the following formula I

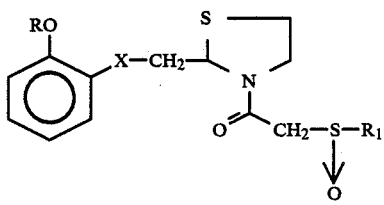

wherein
R is H, $C_1$-$C_4$-alkyl, allyl or propargyl;
X is O, $CH_2$ or S;
$R_1$ is $C_1$-$C_6$-linear or branched alkyl, phenyl, benzyl, or a group of formula $CH_2$—$CH_2$—O—$(CH_2$—$CH_2$—O$)_n$—Ra wherein n is zero or an integer from 1 to 3 and Ra is H, benzyl, or $C_1$-$C_6$-linear or branched alkyl.

The invention concerns also the optical antipodes, i.e. the enantiomers, the racemic mixtures, the geometrical isomers, the diastereoisomers as well as mixtures thereof, of compounds of formula I.

The thiazolidone ring of the compounds I contains in fact an asymmetric carbon atom and a further center of asymmetry is introduced by the sulphinyl group.

Examples of particularly preferred compounds of the invention are the following:

3(R,S)methylsulphinylacetyl-2-(R,S)(2-methoxyphenoxymethyl)-thiazolidine;

3(R,S)methylsulphinylacetyl-2-(R)(2-methoxyphenoxymethyl)-thiazolidine;

3(R,S)methylsulphinylacetyl-2-(S)(2-methoxyphenoxymethyl)-thiazolidine;

3(R)methylsulphinylacetyl-2-(S)(2-methoxyphenoxymethyl)-thiazolidine;

3(S)methylsulphinylacetyl-2-(S)(2-methoxyphenoxymethyl)-thiazolidine;

3(R)methylsulphinylacetyl-2-(R)(2-methoxyphenoxymethyl)-thiazolidine;

3(S)methylsulphinylacetyl-2-(S)(2-methoxyphenoxymethyl)-thiazolidine;

3(R,S)[methoxy-diethoxy-ethylsulphinylacetyl]-2-(R,S)(2-methoxyphenoxymethyl)-thiazolidine;

[(3',6',9'-trioxa)decylsulphinylacetyl]-2(R,S)(2-methoxyphenoxymethyl)-thiazolidine;

3(R,S)ethylsulphinylacetyl-2-(R,S)(2-methoxyphenoxymethyl)-thiazolidine.

The compounds of the invention are prepared by a process comprising the reaction of a compound of formula II

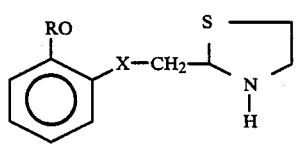

wherein X and R are as above defined, with an activated form of sulphinylacetyl acid of formula III

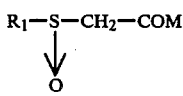

wherein M is selected in the group of 1-imidazolyl, azide

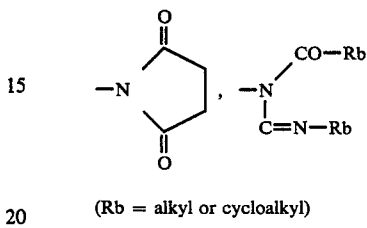

(Rb = alkyl or cycloalkyl)

or the acyl residue of a mixed anhydride.

The acylation of the compounds II with an acylating agent III may be carried out using both stoichiometrical quantities or a slight excess of acylating agent in an inert solvent optionally in the presence of a base.

Each reagent, if desired, may be used in enantiomeric pure form so as to obtain single optical antipodes, or one reagent may be used as a racemic mixture and the other one in enantiomeric form, thus forming a diastereoisomer mixture that may be separated into the single diastereoisomers by crystallization or chromatography.

If both the species are used in the acylating reaction as racemates, the obtained product is a diastereoisomeric racemic mixture.

When compounds II are used in their optically active form, they are preferably used as salts, in the presence of catalytic and stoichiometrical amounts of a base such as alkylamine, imidazole, 4-dimethylaminopyridine, etc.

Preferred salts of compounds II are those obtained by optically active organic acids, commonly used in the resolution of compounds II themselves.

Particularly preferred salts are D(+) or L(—)-O,O'-dibenzoyltartrate.

Preferred inert solvents are chlorinated solvents such as dichloromethane, 1,2-dichloroethane, chloroform; esters, such as ethyl acetate and ethyl formate; ethers such as diethylether, 1,2-dimethoxyethane, dimethylale, tetrahydrofurane, dioxane and mixtures thereof.

The reaction temperature is ranging from −10° C. to the solvent's boiling point, but preferably from −10° C. to the room temperature, whereas the reaction time is ranging from some tenths of minutes to 2 days, but normally it is ranging from 1 to 5 hours.

Compounds of formula II have been described in patent applns. GB 84-19254 (27.7.1984) and GB 85-17553 (11.7.1985).

The acids of formula IV

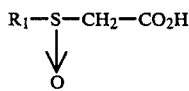

are known compounds or they are prepared using widely known methods, such as the reaction of a halo-compound or an alkyl tosylate

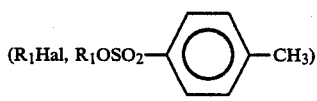

with an alkaline or earth-alkaline thiolate prepared from a thiol of formula $R_1SH$ with an α-halogen-acetic acid or esters thereof to give a sulfide of formula V

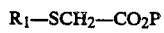

$$R_1-SCH_2-CO_2P \qquad V$$

wherein $R_1$ is as above specified and P is hydrogen or lower alkyl: when P is lower alkyl, a saponification is carried out and the obtained free acids V (P=H) are selectively oxidized according to methods known in the art ($NaIO_4$, equimolecular amounts of $H_2O_2$, methods of microbiological oxidation, Sharpless's methods) to give the sulphinylacetic acids of formula IV that may be then subjected to optical resolution using conventional methods, such as crystallization of salts with chiral amines and/or chromatographic separation on chiral phases.

Acids of formula IV are then converted into the activated acylating forms of formula III using conventional methods. Racemic and optically active dicyclohexylammonium alkylsulphinylacetates and solvents for their crystallization (where alkyl is methyl, ethyl, propyl) are described for example by E. A. Barnsley, Tetrahedron 24, 3747, 1968. Teachings for preparation of sulphinylacetic acids and for their optical separation are given in French patent application No. 7719166 in the name of Asahi Kasei Kogyo Kabushiki Kaisha. In said application, the preparation of activated forms of said acids of formula III is also described.

The compounds of the invention may be used as antitussive agents, or as fluidifying agents for bronchial secretions, and as antiinflammatory agents.

In particular, the compounds of the invention are useful for treating bronchial hyper-reactivity that seems to be a consequence of inflammatory conditions of the trachea and respiratory apparatus.

The most important inflammatory transformations are infiltrations of eosinophiles, desquamation of wide areas of respiratory epithelium, accompanied by hypersecretion of mucus and by hyperplasia of bronchial smooth muscles.

The compounds of the invention are particularly useful in preventing these manifestations induced experimentally. For the foreseen therapeutic uses, the compounds of the invention are suitably formulated into pharmaceutical compositions using conventional techniques and excipients, as described in "Remington's Pharmaceutical Sciences Handbook", Hack Publishing Co., New York, U.S.A. Examples of said compositions include capsules, tablets, sachets, syrups, solutions, suppositories, vials for parenteral or inhalatory administration, optionally controlled-release forms, etc.

The posology may depend on several factors, such as seriousness of the disease and patient's conditions (sex, weight and age): it will normally be included between 100 and 2.000 mg per day, optionally subdivided into several administrations. Higher dosages, even for prolonged periods, may be administered, considering the limited toxicity of the compounds of the invention.

The following examples further illustrate the invention without limiting it.

EXAMPLE 1

A solution of D(+)-O,O'-dibenzoyl tartaric acid.$H_2O$ (76.7 g) in ethyl acetate (560 ml) is added to a solution of 2(±)-(2-methoxyphenoxymethyl)-1,3-thiazolidine (45 g) in ethyl acetate (560 ml).

A precipitate is separated and filtered (55 g), and recrystallized from ethyl acetate (600 ml) at 40° C. to give, after cooling, filtration and drying under vacuum (3 hours, 45° C., 15 mmHg), 49.5 g of (+)2-(2-methoxyphenoxymethyl)-1,3-thiazolidinium-D-(+)-O,O'-dibenzoylmonotartrate, m.p. 127°–129° C., $[α]_D = +77°$ (C=3% in ethanol).

EXAMPLE 2

Using in the procedure of example 1, L(−)O,O'-dibenzoyltartaric acid.$H_2O$, a (−)2-(2-methoxyphenoxymethyl)-1,3-thiazolidinium-L(−)-O,O'-dibenzoylmonotartrate, m.p. 126°–128° C. $[α]_D = -76°$ (C=3% in ethanol), is obtained.

Similarly, the following compounds are subjected to optical resolution:

2(±)-(2-hydroxyphenoxymethyl)-1,3-thiazolidine;
2(±)-(2-allyloxyphenoxymethyl)-1,3-thiazolidine;
2(±)-(2-propargyloxyphenoxymethyl)-1,3-thiazolidine;
2(±)-(2-methoxyphenylthiomethyl)-1,3-thiazolidine;
2(±)-(2-hydroxyphenethyl)-1,3-thiazolidine;
2(±)-(2-methoxyphenethyl)-1,3-thiazolidine; obtaining the corresponding thiazolidine salts with (+) and (−) dibenzoyltartaric acids.

EXAMPLE 3

A solution, cooled with an external bath at 10°–20° C., of carbon tetrabromide (4.74 g) and triethylenglycol monoethylether (2.14 g) in dichloromethane (15 ml) is treated under stirring during 30 minutes with small portions of triphenylphosphine (3.7 g).

Stirring is continued for 60 minutes, the reaction mixture is then evaporated under vacuum. The residue is suspended in a mixture of hexane/diethylether (50/50, 30 ml); the slightly soluble triphenylphosphoxide is filtered and the organic solution is evaporated under vacuum (11 mm Hg at 60° C.) to give 3,6,9-trioxadecylbromide (2.3 g) as an uncoloured oil.

A solution of this compound in ethanol (30 ml) is treated with thiourea (0.8 g) and the mixture is refluxed for 4 hours. The solvent is then evaporated under vacuum to give a solid residue (3,6,9-trioxa-decyl-isothiouronium bromide), that is suspended in deaerated N NaOH (10.5 ml).

Under nitrogen atmosphere, the suspension is refluxed until complete solution. The warm solution is filtered, cooled, treated with 1 g of NaCl and finally acidified to pH 4,5–5 by adding a saturated aqueous solution of $NaH_2PO_4$.

The reaction mixture is then extracted with ethyl acetate: the organic extracts are collected, dried on $Na_2SO_4$, and the solvent is evaporated to give 3,6,9-trioxa-decylmercaptane (1.26 g) as an uncoloured oil. A solution of this compound in methanol (3 ml) is added to a solution of sodium methylate (0.42 g) in methanol (6 ml), and cooled to 0°–5° C. Under stirring, 0.7 g of methyl α-chloroacetate are added in 15 minutes.

The mixture is then warmed to 40° C. for 1 hour, until reaction is completed and methyl 3,6,9-trioxa-decylmercaptoacetate is obtained. The reaction mixture is diluted with aqueous NaOH (7 ml) and warming is prosecuted for 1 hour.

The excess methanol is then evaporated under vacuum, the aqueous residue is acidified to pH 1 by addition of 2N sulphuric acid and, after addition of an excess NaCl, the aqueous phase is extracted more times with ethyl acetate to give, after the usual work-up, a residue of 3,6,9-trioxa-decylmercaptoacetric acid as an uncoloured oil.

EXAMPLE 4

8.1 g of 2-chloro-ethanol are added in an hour to a solution of 9.2 g of thioglycolic acid in 1N NaOH (120–200 ml). The mixture is stirred for 4 hours, then it is acidified to pH 3 with 4N sulphuric acid, and the solution after salting, is thoroughly extracted with ethyl acetate.

The organic phase, after usual work-up, is dried, the solvent evaporated and the residue dried under vacuum, to give a (2-hydroxyethyl)mercapto acetic acid.

Using in this procedure the 3,6-dioxaheptylbromide or 10-phenyl-3,6,9-trioxa-decylbromide, the 3,6-dioxa-heptylmercapto-acetic and 10-phenyl-3,6,9-trioxa-decylmercapto-acetic acids are respectively obtained.

EXAMPLE 5

A solution of methyl 3,6-dioxa-heptylmercaptoacetate (2 g) obtained by esterification of the corresponding acid, prepared in accordance with the examples 4 and 3, is treated in methanol (20 ml) at room temperature, with 2.1 g of sodium periodate in small portions and stirred overnight.

The precipitate is filtered, the alcoholic solution is diluted with water and extracted with ethyl acetate.

The organic phases are collected and after the usual work-up give 1.82 g of methyl (R,S)-3,6-dioxa-heptylsulphinyl acetate that is hydrolyzed by treatment with LiOH (0.4 g) in 10 ml of $H_2O$ for 6 hours at room temperature.

The aqueous phase is extracted with diethylether to remove traces of non-hydrolyzed ester, concentrated under vacuum, acidified with an excess of a $NaH_2PO_4$ saturated solution and extracted with tetrahydrofurane.

The organic extracts are mixed, dried and the residue is triturated with acetone-hexane, yielding 1.14 g of (R,S)-3,6-dioxa-heptyl-sulphinyl acetic acid.

EXAMPLE 6

A solution of methylmercaptoacetic acid (50 g) in acetone under stirring at a temperature lower than 30° C., kept by means of an external ice bath, is added dropwise with hydrogen peroxide 36% (p/v) (50 ml). Stirring is continued for other 2 hours at room temperature, then the excess hydrogen peroxide is decomposed by adding Pd/C 5% (0.5 g). Decomposition of the reagent is complete after some hours of stirring at room temperature, and if desired, to speed up the decomposition itself, the reaction mixture can be heated to 40° C. for 15 minutes.

The catalyst is filtered off and repeatedly washed with acetone, the eluates are collected, and the solvent is then evaporated under vacuum, to give an oily residue, that is dissolved in warm acetone (70 ml). By cooling, (R,S)-methylsulphinyl acetic acid crystallizes, m.p. 85°–87° C. (see also Tanager, Ark. Kemi 24A No. 10 (1947)4, Chem. Abstracts 1948, 8786; N. K. Sklan and E. A. Barnsley, Biochem. J., 107, 217, 1968).

EXAMPLE 7

Using in the procedure of example 6 the acids: (2-hydroxyethyl)mercapto-acetic; 3,6-dioxa-heptyl-mercapto-acetic, 3,6,9-trioxa-decyl-mercapto-acetic; 10-phenyl-3,6,9-trioxa-decyl-mercapto-acetic in substitution of methylmercaptoacetic acid, the following (R,S)-sulphinyl acetic acids are prepared:
2-hydroxyethyl sulphinyl acetic;
3,6-dioxa-heptyl-sulphinylacetic;
3,6,9-trioxa-decyl-sulphinyl acetic;
10-phenyl-3,6,9-trioxa-decyl-sulphinylacetic.

EXAMPLE 8

A solution of N,N'-dicyclohexyl-carbodiimide (10.1 g) in dry 1,2-dimethoxyethane (20 ml) is added to a solution of (R,S)-methylsulphinylacetic acid (6 g) and of 2-(R,S)-(2-methoxyphenoxymethyl)-1,3-thiazolidine (10 g) in dry 1,2-dimethoxyethane (200 ml), under stirring in about 30 minutes. Stirring is continued for further 2 hours, and then the excess carbodiimide is decomposed by adding a 5% oxalic acid solution (5 ml).

Stirring is continued for one hour again, and the precipitate of dicyclohexylurea is filtered off. The filtered solution is concentrated to dryness. The solid residue is dissolved in ethyl acetate (150 ml).

After cooling, a crystalline precipitate is separated that, after recrystallization from ethyl acetate, gives 12 g of 3(R,S)-methylsulphinyl-acetyl-2-(R,S)-(2-methoxyphenoxymethyl)-thiazolidine, m.p. 94°–102° C.

EXAMPLE 9

Using in the procedure of example 8 the following thiazolidines:
2-(R,S)-(2-hydroxyphenoxymethyl)-1,3-thiazolidine;
2-(R,S)-(2-propargyloxyphenoxymethyl)-1,3-thiazolidine;
2-(R,S)-(2-allyloxyphenoxymethyl)-1,3-thiazolidine;
2-(R,S)-(2-methoxyphenylthiomethyl)-1,3-thiazolidine;
2-(R,S)-(2-methoxyphenethyl)-1,3-thiazolidine;
2-(R,S)-(2-hydroxyphenethyl)-1,3-thiazolidine; the following compounds were prepared:
3-(R,S)-methylsulphinyl-acetyl-2-(R,S)-(2-hydroxyphenoxymethyl)-1,3-thiazolidine;
3-(R,S)-methylsulphinyl-acetyl-2-(R,S)-(2-propargyloxyphenoxymethyl)-1,3-thazolidine;
3-(R,S)-methylsulphinyl-acetyl-2-(R,S)-(2-allyloxyphenoxymethyl)-1,3-thazolidine;
3-(R,S)-methylsulphinyl-acetyl-2-(R,S)-(2-methoxyphenylthiomethyl)-1,3-thazolidine;
3-(R,S)-methylsulphinyl-acetyl-2-(R,S)-(2-methoxyphenethyl)-1,3-thazolidine;
3-(R,S)-methylsulphinyl-acetyl-2-(R,S)-(2-hydroxyphenethyl)-1,3-thazolidine;

EXAMPLE 10

Small portions of 1,1-carbonyl-diimidazole (1.6 g) are added in 30' to a suspension of (R)-methyl-sulphinyl acetic acid (1.2 g) in anhydrous tetrahydrofurane (10 ml). A clear solution of R-methylsulphinyl-acetyl-imidazolide is obtained which is added to a suspension in anhydrous tetrahydrofurane (40 ml) of 2(R)(2-methoxyphenoxymethyl)-1,3-thiazolidine, D(+)-O,O'-dibenzoylmonotartrate prepared in accordance with example 1, vigorously stirred and cooled at 5°–15° C.

Stirring is prosecuted for about 1 hour, the solvent is evaporated under vacuum and the residue is partitioned between water and dichloromethane.

The organic phase is washed with a 5% NaHCO₃ aqueous solution and water, dried on Na₂SO₄ and evaporated to dryness. The residue is crystallized from isopropyl ether/ethyl acetate to give 1.9 g of 3(R)-methylsulphinylacetyl-2-(R)-(2-methoxyphenoxymethyl)-1,3-thiazolidine; m.p. 120°–121° C.

In the same way, using the suitable optical antipodes, the following compounds were obtained:

3(R)methylsulphinylacetyl-2(S)-(2-methoxyphenoxymethyl)-1,3-thiazolidine;

3(S)methylsulphinylacetyl-2(S)-(2-methoxyphenoxymethyl)-1,3-thiazolidine;

3(S)methylsulphinylacetyl-2(R)-(2-methoxyphenoxymethyl)-1,3-thiazolidine;

EXAMPLE 11

Ethyl chloroformate (1.1 g) is added dropwise to a cooled and stirred solution on triethylamine (1 g) and (R,S)-methylsulphinylacetic acid (1.2 g) in anhydrous tetrahydrofurane, in 30 minutes.

Stirring is prosecuted for further 30 minutes so as to complete formation of the mixed anhydride, which is then added under vigorous stirring to a cooled solution (−10° C.) of triethylamine (1 g) and 2(R)-(2-methoxyphenoxymethyl)-1,3-thiazolidine-D(+)-O,O'-dibenzoylmonotartrate (5.5 g) in dry tetrahydrofurane (50 ml). Stirring is continued for 30 minutes at −10° C., then the cooling bath is removed and stirring is prosecuted again for 30′ at room temperature.

After evaporation under vacuum of the solvent, the residue is partitioned between water and ethyl acetate; the organic phase is separated and washed with 5% NaHCO₃, water and then dried. 3-(R,S)-methyl-sulphinylacetyl-2(R)-(2-methoxyphenoxymethyl)-1,3-thiazolidine, m.p. 113°–115° C.; [α] = +76° (C=1%, ETOH) crystallizes after concentration of the solvent.

In the same way, 3(R,S)-methylsulphinylacetyl-2-(S)-2-methoxyphenoxymethyl)-1,3-thiazolidine is obtained, m.p. 111°–114° C. [α]$_D$= −72° (C=1% ETOH), using in the above procedure a 2(S)-(2-methoxyphenoxymethyl)-1,3-thiazolidine-L(−)-O,O-dibenzoyltartrate.

EXAMPLE 12

Using in procedures of examples 8, 10 and 11, a 2(R,S)-(2-methoxyphenoxymethyl)-thiazolidine, 2(R)(2-methoxyphenoxymethyl)thiazolidine-D(+)-O,O'-dibenzoylmonotartrate or 2(S)(2-methoxyphenoxymethyl)thiazolidine-L(−)O,O'-dibenzoyl-monotartrate and a sulphinylacetic acid selected in the group of (R,S)-ethylsulphinylacetic
(R)-ethylsulphinylacetic
(S)-ethylsulphinylacetic
(R,S)-propylsulphinylacetic
(R)-propylsulphinylacetic
(S)-propylsulphinylacetic
(R,S)-(2-hydroxyethyl)sulphinylacetic
(R,S)-3,6-dioxa-heptyl-sulphinylacetic
(R,S)-3,6,9-trioxa-decylsulphinylacetic
(R,S)-10-phenyl-3,6,9-trioxa-decylsulphinylacetic acids, the following 3-sulphinylacetyl-thiazolidines were obtained:

3-(R,S)-ethylsulphinylacetyl-2-(R,S)-(2-methoxyphenoxymethyl)-1,3-thiazolidine;

3-(R,S)-ethylsulphinylacetyl-2-(R)-(2-methoxyphenoxymethyl)-1,3-thiazolidine;

3-(R)-ethylsulphinylacetyl-2-(R)-(2-methoxyphenoxymethyl)-1,3-thiazolidine;

3-(S)-ethylsulphinylacetyl-2-(R)-(2-methoxyphenoxymethyl)-1,3-thiazolidine;

3-(R,S)-propylsulphinylacetyl-2-(R,S)-(2-methoxyphenoxymethyl)-1,3-thiazolidine;

3-(R,S)-propylsulphinylacetyl-2-(R)-(2-methoxyphenoxymethyl)-1,3-thiazolidine;

3-(R)-propylsulphinylacetyl-2-(R)-(2-methoxyphenoxymethyl)-1,3-thiazolidine;

3-(S)-propylsulphinylacetyl-2-(R)-(2-methoxyphenoxymethyl)-1,3-thiazolidine;

3-(R,S)-(2-hydroxyethylsulphinylacetyl)-2-(R,S)-(2-methoxyphenoxymethyl)-1,3-thiazolidine;

3-(R,S)-(2-hydroxyethylsulphinylacetyl)-2-(R)-(2-methoxyphenoxymethyl)-1,3-thiazolidine;

3-(R,S)-(3,6-dioxaheptylsulphinylacetyl)-2-(R,S)-(2-methoxyphenoxymethyl)-1,3-thiazolidine;

3-(R,S)-(3,6-dioxaheptylsulphinylacetyl)-2-(R)-(2-methoxyphenoxymethyl)-1,3-thiazolidine;

3-(R,S)-(3,6,9-trioxadecylsulphinylacetyl)-2-(R,S)-(2-methoxyphenoxymethyl)-1,3-thiazolidine;

3-(R,S)-(3,6,9-trioxadecylsulphinylacetyl)-2-(R)-(2-methoxyphenoxymethyl)-1,3-thiazolidine;

3-(R,S)-(10-phenyl-3,6,9-trioxadecylsulphinylacetyl)-2-(R,S)-(2-methoxyphenoxymethyl)-1,3-thiazolidine;

3-(R,S)-(10-phenyl-3,6,9-trioxadecylsulphinylacetyl)-2-(R)-(2-methoxyphenoxymethyl)-1,3-thiazolidine.

EXAMPLE 13

A solution of sodium thiophenate (13.2 g) in methanol is reacted with 10.9 g of methyl α-chloroacetate to give, after ester hydrolysis with aqueous NaOH 0.5N, 14.8 g of phenylthioacetic acid, that is then transformed by reaction with hydrogen peroxide in acetone in (R,S)-phenyl-sulphinylacetic acid (13 g).

Similarly, from benzylchloride and thioglycolic acid and subsequent oxidation with hydrogen peroxide, a (R,S)-phenylmethylsulphinyl acetic acid is obtained. Using said acid in the procedure of example 11, the following compounds were prepared:

3(R,S)-(phenylsulphinylacetyl)-2-(R)-(2-methoxyphenoxymethyl)-1,3-thiazolidine; [α]$_D$= +68° (c=2% in ethanol);

3-(R,S)-(benzylsulphinylacetyl)-2-(R)-(2-methoxyphenoxymethyl)-1,3-thiazolidine; [α]$_D$= +69° (c=2% in ethanol).

What is claimed is:

1. Compounds of formula I

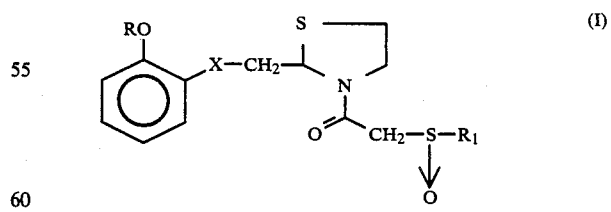

wherein
R is H, $C_1$–$C_4$-alkyl, allyl or propargyl;
X is O, $CH_2$ or S;
$R_1$ is $C_1$–$C_6$-linear or branched alkyl, phenyl, benzyl, or a group of formula $CH_2$—$CH_2$—O—($CH_2$—$CH_2$—O)$_n$—Ra wherein n is zero or an integer from 1 to 3 and Ra is H, benzyl or $C_1$–$C_6$-linear or branched alkyl, their enantiomers, diastereoisomers and mixtures thereof.

2. Compounds according to claim 1 wherein X is oxygen.

3. Compound according to claim 1, selected in the group consisting of:

3(R,S)methylsulphinylacetyl-2-(R,S)(2-methoxyphenoxymethyl)-thiazolidine;
3(R,S)methylsulphinylacetyl-2-(R)(2-methoxyphenoxymethyl)-thiazolidine;
3(R,S)methylsulphinylacetyl-2-(S)(2-methoxyphenoxymethyl)-thiazolidine;
3(R)methylsulphinylacetyl-2-(S)(2-methoxyphenoxymethyl)-thiazolidine;
3(S)methylsulphinylacetyl-2-(S)(2-methoxyphenoxymethyl)-thiazolidine;
3(R)methylsulphinylacetyl-2-(R)(2-methoxyphenoxymethyl)-thiazolidine;
3(S)methylsulphinylacetyl-2-(S)(2-methoxyphenoxymethyl)-thiazolidine;
3(R,S)[methoxy-diethoxy-ethylsulphinylacetyl]-2-(R,S)-(2-methoxyphenoxymethyl)-thiazolidine;
[(3',6',9'-trioxa)decylsulphinylacetyl)]-2(R,S)(2-methoxyphenoxymethyl)-thiazolidine;
3(R,S)ethylsulphinylacetyl-2-(R,S)(2-methoxyphenoxymethyl)-thiazolidine.

4. Pharmaceutical composition for use as an antitussive agent, as a fluidifying agent for bronchial secretions, and/or as an anti-inflammatory agent, said composition comprising a pharmaceutically effective amount of a compound of claim 1, 2 or 3 and a pharmaceutically acceptable vehicle therefore.

5. The method of producing an antitussive, mucus-fluidifying, or anti-inflammatory effect in a patient in need of such effect, said method comprising administering to said patient an effective amount of a compound of claim 1, 2 or 3.

* * * * *